US00PP29982P2

(12) United States Plant Patent
Horvath

(10) Patent No.: US PP29,982 P2
(45) Date of Patent: Dec. 11, 2018

(54) ***MONARDA* HYBRID PLANT NAMED 'MOJO'**

(50) Latin Name: ***Monarda* hybrid**
Varietal Denomination: Mojo

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 15/530,337

(22) Filed: Dec. 28, 2016

(51) Int. Cl.
*A01H 5/02* (2018.01)

(52) U.S. Cl.
USPC ..... Plt./455
CPC ..... *A01H 5/02* (2013.01)

(58) Field of Classification Search
USPC ..... Plt./455
CPC ..... A01H 5/02
See application file for complete search history.

*Primary Examiner* — Kent L Bell

(57) ABSTRACT

A new, distinct *Monarda* hybrid plant as shown and described, characterized by the combination of purple colored new growth, purple flowers, and plants that are resistant to powdery mildew.

2 Drawing Sheets

Figure 1:
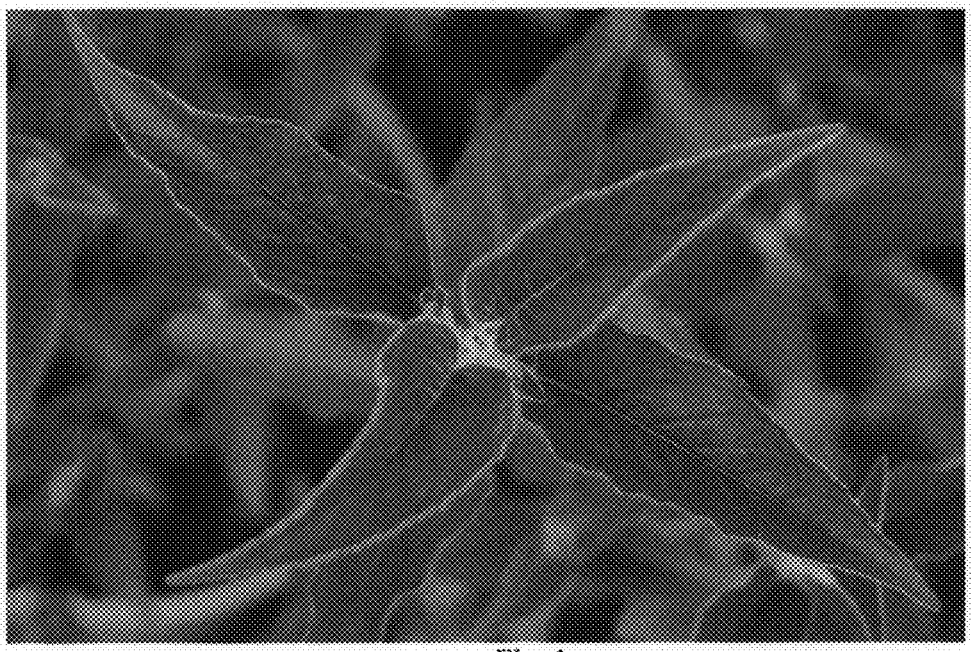

Latin name: *Monarda* hybrid.
Cultivar name: 'Mojo'.

BACKGROUND OF THE INVENTION

The present invention relates to a new and distinct cultivar of *Monarda* plant, botanically known as *Monarda* hybrid and hereinafter referred to by the name 'Mojo'. The new *Monarda* plant is a product of a planned breeding program conducted by the Inventor in Hebron, Ill., USA. The objective of the breeding program is to create new *Monarda* plants that are resistant to powdery mildew. The new *Monarda* plant was discovered and selected by the Inventor as a single flowering plant from within the progeny of the stated cross-pollination of an unnamed plant of *Monarda bradburiana* as the female patent and an unnamed plant of *Monarda fistulosa* as the male parent, grown in a controlled environment in Hebron, Ill., USA during the summer of 2014. Asexual reproduction of the new *Monarda* plant by softwood cuttings in Hebron, Ill., USA since the summer of 2015, has shown that the unique features of this new *Monarda* plant are stable and reproduced true to type in successive generations. No plants of the new *Monarda* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

Plants of the new *Monarda* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Mojo'.

These characteristics in combination distinguish 'Mojo' as a new and distinct *Monarda* plant:

1. 200 A new growth.
2. Purple-colored N78 B flowers.
3. Resistant to powdery mildew.

Plants of the new *Monarda* differ primarily from plants of 'Pink Lace' U.S. Plant Pat. No. 18,367 in the following characteristics:

1. Plants of the new *Monarda* are taller than plants of 'Pink Lace'.
2. Flowers of plants of the new *Monarda* are darker in color than flowers of plants of 'Pink Lace'.

Plants of the new *Monarda* can be compared to plants of the female parent an unnamed plant of *Monarda bradburiana.*

In side-by-side comparisons plants of the new *Monarda* differ from plants of an unnamed plant of *Monarda bradburiana* in the following characteristics:

1. Plants of the new *Monarda* are more upright and taller than plants of an unnamed plant of *Monarda bradburiana.*
2. Flowers of plants of the new *Monarda* are darker in color than flowers of plants of an unnamed plant of *Monarda bradburiana.*

Plants of the new *Monarda* can be compared to plants of the male parent an unnamed plant of *Monarda fistulosa.*

In side-by-side comparisons plants of the new *Monarda* differ from plants of the unnamed plant of *Monarda fistulosa* in the following characteristics:

1. Plants of the new *Monarda* are shorter than plants of the unnamed plant of *Monarda fistulosa.*
2. Flowers of plants of the new *Monarda* are lighter in color than the purple flowers of plants of the unnamed plant of *Monarda fistulosa.*

DESCRIPTION OF PHOTOGRAPHS

The accompanying colored photographs illustrate the overall appearance of the new *Monarda* plant showing the colors as true as it is reasonably possible to obtain in colored reproductions of this type. Colors in the photographs may differ slightly from the color values cited in the detailed botanical description which accurately describe the actual colors of the new *Monarda* plant.

FIG. 1. Close up of the new foliage on a one year old plant in Hebron, Ill. USA.

Figure 2:
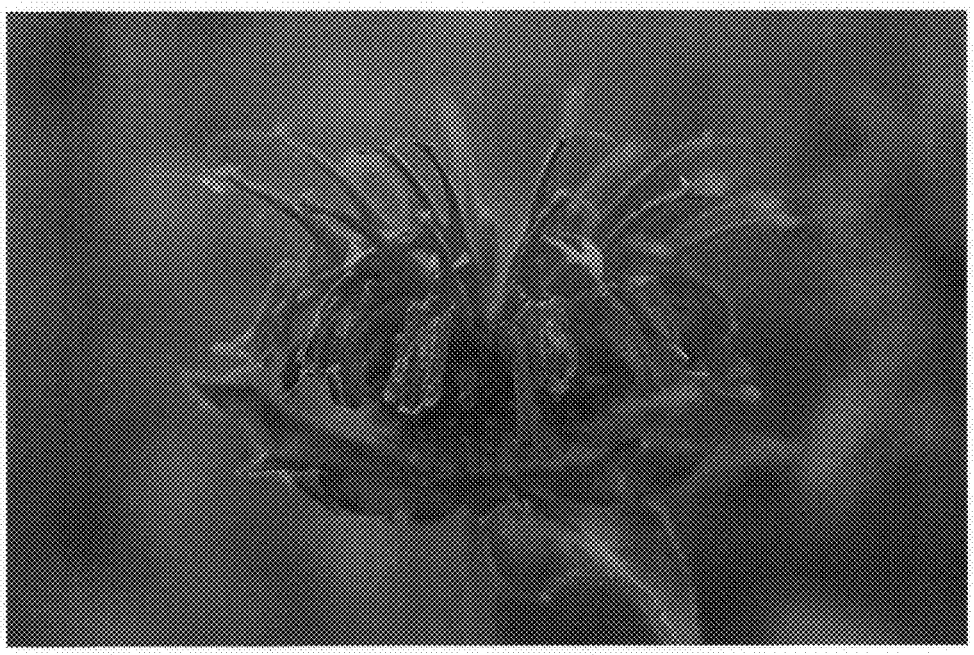

FIG. 2. Close up flower in June on a one year old plant in Hebron, Ill. USA.

Figure 3:
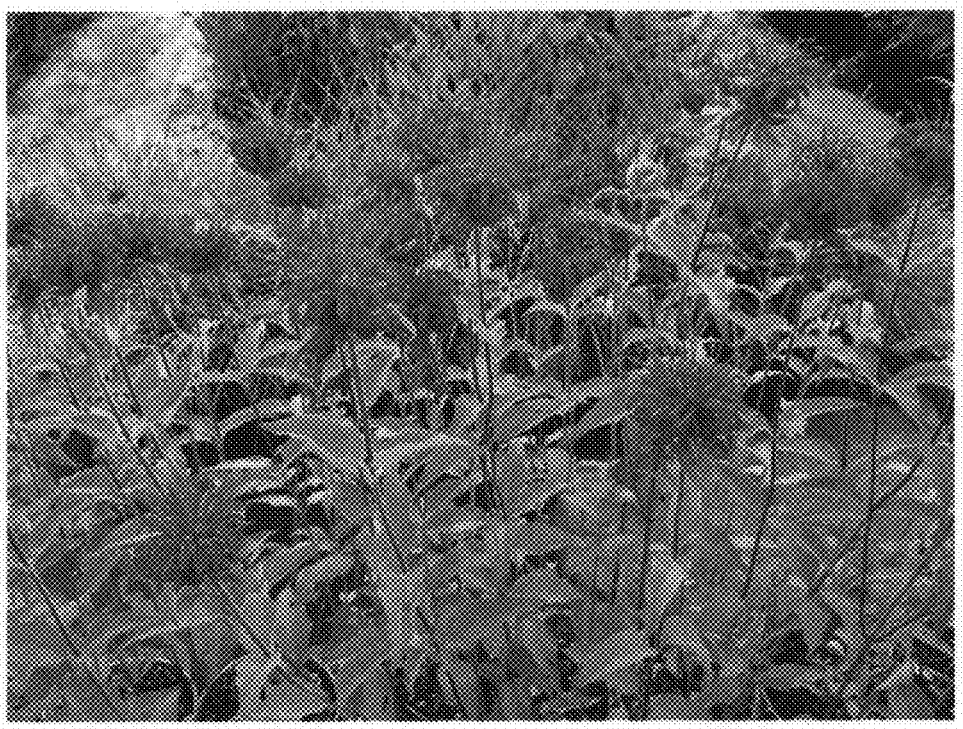

FIG. 3. One gallon, Blooming plants in June on one year old plants in Hebron, Ill. USA.

DETAILED BOTANICAL DESCRIPTION

The aforementioned photographs and following observations, measurements and values describe one year old plants grown during the summer in an outdoor nursery in Hebron, Ill. USA and under typical production conditions. In the detailed description, color references are made to The Royal Horticultural Society Colour Chart, 2001 Edition, except where general terms of ordinary dictionary significance are used.

Plant description:

Botanical classification: *Monarda* hybrid.

Parentage:

*Female, or seed, parent.*—*Monarda bradburiana*, unnamed seedling.

*Male, or pollen, parent.*—*Monarda fistulosa*, unnamed seedling.

Propagation:

*Type cutting.*—By softwood cuttings.

*Time to initiate roots, summer.*—About two weeks.

*Time to produce a rooted young plant, summer.*—About two months.

*Root description.*—Fine, fibrous; grey brown in color.

*Rooting habit.*—Freely branching; dense.

Plant description:

*Plant and growth habit.*—Perennial, upright and outwardly spreading plant form; broad; basal branching habit; moderately vigorous growth habit.

*Plant height.*—60 cm.

*Plant width.*—50 cm.

*Lateral branch description.*—Length: About 25 cm. Diameter: About 3 mm.

Internode length: About 5 cm. Strength: Strong. Aspect: Upright. Texture: Slightly pubescent. Color: 200 B.

Foliage description:

*Arrangement.*—Opposite, simple.

*Length.*—About 77 mm.

*Width.*—About 5 cm.

*Shape.*—Ovate.

*Apex.*—Acute.

*Base.*—Rounded to truncate.

*Margin.*—Serrate.

*Texture, upper and lower surfaces.*—Slightly rugose; pubescent.

*Venation pattern.*—Pinnate.

*Color.*—Developing leaves, upper surface: 200 A. Developing leaves, lower surface: N79 A. Mature leaves, upper surface 137 B, Mature leaf, lower surface 191 A.

*Petiole size.*—Length. — About 23 mm and diameter. — About 2 mm.

*Petiole color, upper surface.*—N186 C, lower surface. — 59 A.

Flower description:

*Flower form, arrangement and flowering habit.*—Single labiate and sessile flowers arranged in terminal globular spikes; flowers face outwardly; freely flowering habit with about 180 flowers developing per inflorescence.

*Natural flowering season.*—Continuous flowering from early June to July in Hebron, Ill., USA.

*Flower longevity on the plant.*—About five days; flowers not persistent.

*Fragrance.*—Faintly fragrant; spicy, pleasant.

*Flower buds.*—Length: About 3 cm. Diameter: About 3 mm. Shape: Narrowly oblanceolate; Curved. Color: N78 B.

*Inflorescence size.*—Length: About 5 cm. Diameter: About 6 cm.

*Inflorescence bracts, typical and observed.*—Arrangement: subtending, Number: 8-10, Shape: ovate, Length: about 4 cm. Width: 15-20 mm, Apex: acute, Margin: entire, Base: truncate, Color: At the base N78 B blending into 137 C at the tips.

*Flowers.*—Diameter: About 3 mm. Depth: About 3 cm.

*Petals.*—Arrangement: Labiate; upper lip hooded; lower lip, a single lobe; lips fused. Length, upper and lower lips: About 3 cm. Width, upper lip: About 1 mm. Width, lower lip: About 4 mm. Shape, upper lip: Lanceolate; apex, narrowly acute. Shape, lower lip: Oblanceolate; apex, aristate. Margin, upper and lower lips: Entire. Texture, upper and lower surfaces: Pubescent. Color: When opening, upper and lower surfaces and when fully opened, upper and lower surfaces: N78 B.

*Sepals.*—Arrangement: Five in a single whorl: fused, tubular. Length: About 9 mm. Width: About 2.5 mm. Apex: Narrowly acute. Margin: Entire. Texture, upper and lower surfaces: Pubescent. Color: When opening, upper and lower surfaces and fully opened, upper and lower surfaces: 137 B with a stripe down the middle toward the base color, N79 D.

*Reproductive organs.*—Stamens: Quantity per flower. Two. Filament length. About 1.5 cm. Filament color: Close to 68 C to 68 D. Anther length: About 2 mm. Anther shape: Narrowly elliptic. Anther color: Close to 71 A. Pollen amount: Scarce. Pollen color: 96 D. Pistils: Quantity per flower: One. Pistil length: About 25 mm. Stigma shape: Cleft. Stigma color: N82 B. Style length: 20 mm Style color N82 B. Ovary color green.

*Seed and fruit.*—Seed and fruit production have not been observed.

Disease resistance: Plants of the new *Monarda* have been observed to be resistant to powdery mildew common to *Monarda* plants.

Pest resistance: Plants of the new *Monarda* have not been observed to be resistant to pests and other pathogens common to *Monarda* plants.

Garden performance: Plants of the new *Monarda* have exhibited good tolerance to rain and wind, have been observed to be hardy to USDA Zone 5 and to tolerate high temperatures of about 35° C.

I claim:

1. A new, distinct *Monarda* hybrid plant as shown and described, characterized by the combination of purple colored new growth, purple flowers, and plants that are resistant to powdery mildew compared to the seed parent.

* * * * *